(12) United States Patent
Arvidsson

(10) Patent No.: US 9,107,639 B2
(45) Date of Patent: Aug. 18, 2015

(54) SYSTEM FOR SYNCHRONOUSLY VISUALIZING A REPRESENTATION OF FIRST AND SECOND INPUT DATA

(75) Inventor: Adam Arvidsson, Malmö (SE)

(73) Assignee: MEDICINSK BILDTEKNIK SVERIGE AB, Lund (SE)

( * ) Notice: Subject to any disclaimer, the term of this patent is extended or adjusted under 35 U.S.C. 154(b) by 13 days.

(21) Appl. No.: 13/048,769

(22) Filed: Mar. 15, 2011

(65) Prior Publication Data

US 2012/0236032 A1   Sep. 20, 2012

(51) Int. Cl.
*A61B 6/00* (2006.01)
*A61B 8/12* (2006.01)
*A61B 8/00* (2006.01)
*G09G 5/00* (2006.01)
*A61B 5/0215* (2006.01)
*A61B 5/00* (2006.01)

(52) U.S. Cl.
CPC ............... *A61B 6/504* (2013.01); *A61B 6/461* (2013.01); *A61B 6/463* (2013.01); *A61B 6/507* (2013.01); *A61B 6/5247* (2013.01); *A61B 8/12* (2013.01); *A61B 8/463* (2013.01); *A61B 5/0215* (2013.01); *A61B 5/6851* (2013.01); *G09G 5/003* (2013.01); *G09G 2352/00* (2013.01); *G09G 2380/08* (2013.01)

(58) Field of Classification Search
CPC ............ G06T 19/00; G06T 2207/10081; G06T 2207/30104; A61B 6/504
USPC .......... 382/128, 130, 132; 345/629, 419, 634; 600/424
See application file for complete search history.

(56) References Cited

U.S. PATENT DOCUMENTS

| | | | |
|---|---|---|---|
| 4,399,457 A * | 8/1983 | Riederer et al. | 378/98.12 |
| 5,282,471 A * | 2/1994 | Sato | 600/443 |
| 5,345,938 A | 9/1994 | Nishiki et al. | |
| 6,442,235 B2 * | 8/2002 | Koppe et al. | 378/62 |
| 6,565,514 B2 | 5/2003 | Svanerudh et al. | |
| 7,840,255 B2 * | 11/2010 | Ichihara | 600/425 |
| 2003/0216621 A1 | 11/2003 | Alpert et al. | |
| 2006/0152516 A1 * | 7/2006 | Plummer | 345/538 |
| 2007/0016029 A1 | 1/2007 | Donaldson et al. | |
| 2007/0041660 A1 * | 2/2007 | Mahesh et al. | 382/294 |
| 2007/0098134 A1 * | 5/2007 | Toyoshima et al. | 378/4 |
| 2007/0255145 A1 | 11/2007 | Smith et al. | |
| 2007/0276270 A1 * | 11/2007 | Tran | 600/508 |
| 2008/0063144 A1 | 3/2008 | Belanger | |
| 2009/0097731 A1 * | 4/2009 | Sanada et al. | 382/132 |
| 2009/0150184 A1 * | 6/2009 | Spahn | 705/3 |
| 2010/0002839 A1 * | 1/2010 | Yokota et al. | 378/98.12 |
| 2010/0053213 A1 * | 3/2010 | Ishida et al. | 345/629 |

(Continued)

FOREIGN PATENT DOCUMENTS

| | | |
|---|---|---|
| WO | 2005024729 A1 | 3/2005 |
| WO | 2006041346 A1 | 4/2006 |
| WO | 2006076409 A2 | 7/2006 |

*Primary Examiner* — James A Thompson
(74) *Attorney, Agent, or Firm* — Capitol City TechLaw

(57) ABSTRACT

A system for synchronous visualization of a representation of first input data and second input data in real time on single display unit is disclosed. The system comprises a control unit for receiving said first and second input data, said control unit being arranged for displaying a synchronous representation of said first and second input data on said display unit. A method for operating the system is also disclosed.

5 Claims, 4 Drawing Sheets
(2 of 4 Drawing Sheet(s) Filed in Color)

(56) References Cited

U.S. PATENT DOCUMENTS

| | | | |
|---|---|---|---|
| 2010/0094124 A1* | 4/2010 | Schoonenberg et al. | 600/424 |
| 2010/0234698 A1* | 9/2010 | Manstrom et al. | 600/301 |
| 2010/0259550 A1* | 10/2010 | Baumgart et al. | 345/589 |
| 2011/0075912 A1* | 3/2011 | Rieber et al. | 382/132 |
| 2011/0245693 A1* | 10/2011 | Hastings et al. | 600/486 |

* cited by examiner

SYSTEM FOR SYNCHRONOUSLY VISUALIZING A REPRESENTATION OF FIRST AND SECOND INPUT DATA

FIELD OF THE INVENTION

The present invention relates to the field of examination of coronary artery diseases. Especially, it relates to a system for the visualization of medical (image) data of the coronary arteries.

BACKGROUND

In coronary artery disease the supply of oxygen rich blood to part(s) of the heart muscle may be partly choked or even totally choked by a narrowing, e.g. stenosis, of one or several coronary arteries. The effect of choked blood flow to the heart spans from pain in the chest (i.e. angina pectoris), to ischemia eventually causing heart failure and possible death.

Historically, it has been thought that detection and quantification of arterial narrowings may be performed by X-Ray angiography alone.

In X-Ray angiography, an image representation of the arteries is obtained after injection of a contrast agent. However, X-Ray angiography is presently not commonly used alone for diagnosing the severity of stenosis. Rather, X-Ray angiography is combined with an intravascular measurement of the pressure and/or blood flow, or combined with intravascular ultrasound.

Intravascular measurements of the pressure and/or blood flow may be performed by use of guide-wire with sensor(s) at the distal end. Typically, the guide-wire with the sensor(s) is inserted into the body via vessels in the groin. The guide-wire, with sensor(s), is normally operatively connected to a control unit receiving input data from the sensor(s). By connecting the control unit to a display unit the pressure may be observed in real time.

Fractional Flow Reserve (FFR) is a ratio which relates to the pressure differences across a coronary artery stenosis (narrowing, usually due to atherosclerosis). From the FFR measured, the likelihood that the stenosis impedes oxygen delivery to the heart muscle, eventually causing myocardial ischemia, may be determined FFR is defined as the pressure behind (distal to) a stenosis relative to the pressure before the stenosis and does thus also relate to the pressure drop over the stenosis. FFR is an absolute number and an FFR of 0.50 is seen if the pressure drop over the stenosis is 50%. Thus, FFR is a comparison of the maximal blood flow in the vessel in the presence of a stenosis compared to the maximal blood flow in the hypothetical absence of the stenosis. Typically, also FFR may be measured by use of guide-wire with sensor(s) at the distal end.

Intravascular ultrasound (IVUS) is a medical imaging methodology using a specially designed catheter with a miniaturized ultrasound probe attached to the distal end of the catheter. The proximal end of the catheter is attached to a computerized ultrasound equipment generating an ultrasound image. By use of IVUS it is possible to "see" from inside blood vessels out through the surrounding blood column, visualizing the endothelium (inner wall) of blood vessels in living individuals.

The arteries of the heart (the coronary arteries) are the most frequent imaging target for IVUS. IVUS may for example be used in the coronary arteries to determine the amount of atheromatous plaque built up at any particular point in the epicardial coronary artery. It is also used to assess the effects of treatment of stenosis, such as with hydraulic angioplasty expansion of the artery, with or without stents, and the results of medical therapy over time.

X-ray angiography imaging is used within the art to monitor the position of an intravascular probe used for measuring of a hemodynamic parameter or for generating an IVUS signal within a blood vessel. An examining physician typically relies on the X-ray angiography imaging to monitor the position for probe used for measuring of a hemodynamic parameter or for generating an IVUS signal; whereby the location of e.g. stenosis of coronary artery may be determined. Hence, intravascular measurements guided by X-ray angiography imaging are useful in diagnosing cardiovascular diseases.

In the art, X-ray angiography imaging data is visualized in real time, separately from the real time representation of an intra vascular hemodynamic parameter, such as the intravascular pressure or flow, or the intravascular ultrasound (IVUS) imaging signal. In order to assist the physician, it would be of value to avoid having to look at separate screens.

The prevalence of cardiovascular disease is rapidly increasing, especially in the western parts of the world. So are the costs for health care. The possibility to scrutinize a diagnosis, or for the examining physician to justify it, afterwards is therefore growing more and more important. There is therefore also a need for a reliable and efficient way of archiving examinations results in the art.

SUMMARY OF THE INVENTION

Accordingly, the present invention preferably seeks to mitigate, alleviate, eliminate or circumvent one or more of the above-identified deficiencies in the art and disadvantages singly or in any combination and solves at least the above mentioned problems by providing a system for synchronous visualization of a representation of first input data and second input data in real time on single display unit, wherein said system comprises a control unit for receiving said first and second input data, said control unit being arranged for displaying a synchronous representation of said first and second input data on said display unit; and a method of synchronously visualizing X-ray imaging data and intra vascular hemodynamic data or intravascular ultrasound (IVUS) imaging data, comprising the steps of: collecting X-ray imaging data and intra vascular hemodynamic data or intravascular ultrasound (IVUS) imaging data from a patient; processing the collected data; and displaying the processed data as a synchronous common representation of the collected data.

Further advantageous features of the invention are defined in the dependent claims and with regard to embodiments disclosed herein

BRIEF DESCRIPTION OF THE DRAWINGS

The file of this patent contains at least one drawing/photograph executed in color. Copies of this patent with color drawings/photographs will be provided by the United States Patent and Trademark Office upon request and payment of the necessary fee.

DESCRIPTION OF EMBODIMENTS

Figure 1:
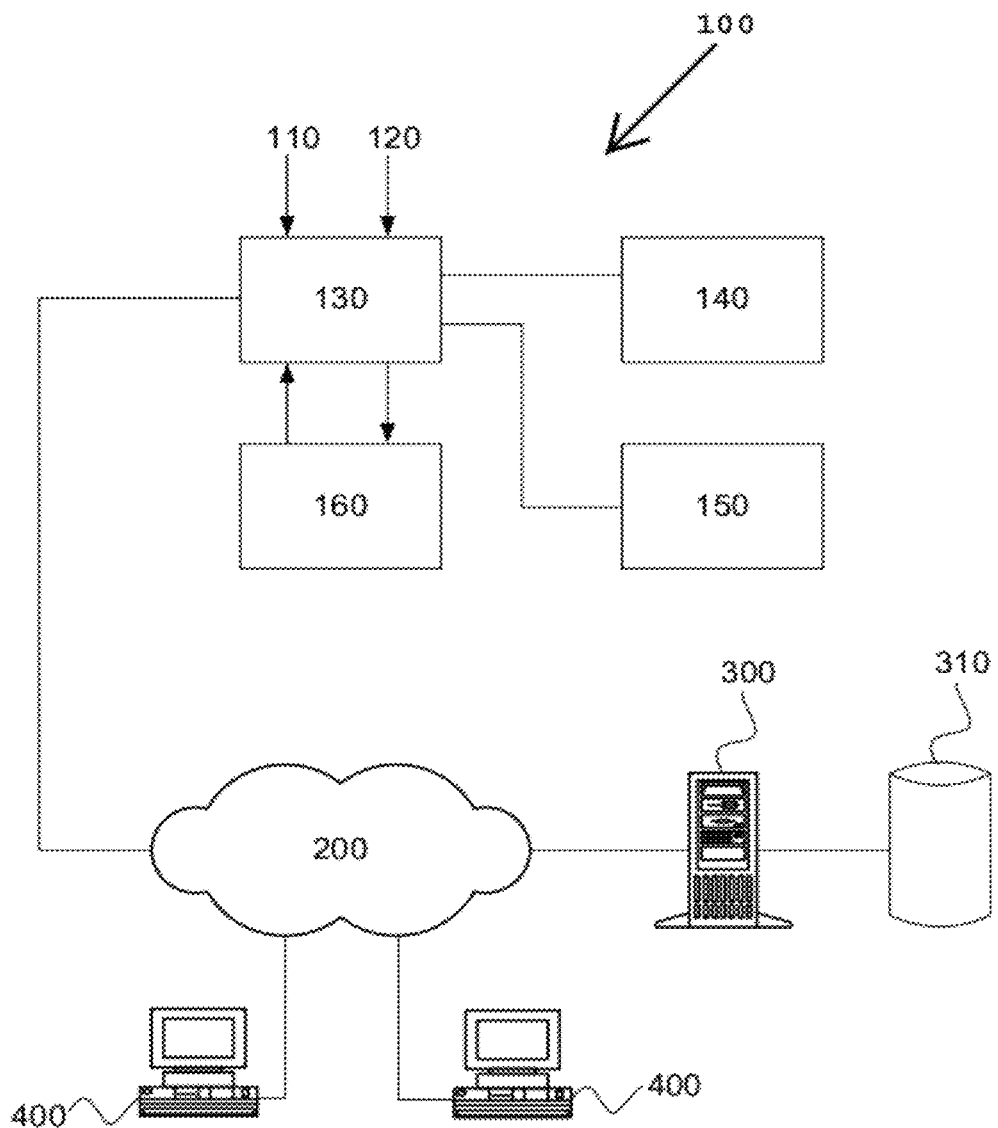
FIG. 1 depicts an overview of a system for synchronous visualization of a representation of first input data and second input data integrated in a network.

An embodiment, in accordance with FIG. 1, relates to a system 100 for synchronous visualization of a representation of first input data 110 and second input data 120 in real time. The first input data 110 is typically X-ray imaging data, such as X-ray angiography imaging data. The X-ray imaging data may be in the form of a high or low resolution analog video signal (e.g. a composite, Y/C, or VGA video signal). Further the X-ray imaging data may be a digital SDI or DVI signal. The second input data 120 is typically data representative for one or several intra vascular hemodynamic parameter(s), such as the intravascular pressure and/or FFR, or an intravascular ultrasound (IVUS) image signal. A second input data representing a vascular hemodynamic parameter may be parameter data or an image signal. Such an image signal may be high or low resolution analog video signal (e.g. a combined, Y/C, or VGA video signal). Further it may be a digital SDI or DVI signal. A second input data being an intravascular ultrasound (IVUS) image signal may be high or low resolution analog video signal (e.g. a composite, Y/C, or VGA video signal). Further it may be a digital SDI or DVI signal. In the system 100, the first and second input data 110, 120 are received by a control unit 130 in real time. Thus, the received first and second input data 110, 120 are inherently synchronized. The control unit 130 is arranged for displaying a synchronous representation of the first and second input data 110, 120 on a single display unit 140, such as a computer or monitor screen.

Displaying a synchronous representation of the first and second input data 110 and 120 on a single display unit 140 implies that the operator, typically a physician, very accurately and in real time may determine relevant cardio vascular parameters, such as the intravascular pressure or the presence of atheromatous plaque, at a given position apparent from the displayed X-ray angiography imaging.

Intravascular measurement of the pressure and/or blood flow may be performed by use of a guide-wire, e.g. catheter, provided with sensor(s) at the distal end. The guide-wire may be inserted into the body via a vessel in the groin. By operatively connecting the sensor(s) via the proximal end of the guide-wire to a control unit, an output signal representing a hemodynamic parameter, such as the intravascular pressure may be obtained. The second input data 120 may be such an output signal representing one or several hemodynamic parameter(s).

A common representation of intra vascular pressure is typically a graph with the variation in pressure over time represented. Commonly, also Fractional Flow Reserve (FFR) may be determined and visualized. The representation of the second input data 120 displayed on the display unit 140 may thus be a graph of the variation in the pressure over time and optionally also the FFR.

An example of a guide-wire with pressure sensor is the PressureWire® from Radi Medical Systems, Uppsala, Sweden. By connecting the proximal end of the PressureWire® to the Radi Analyzer®, also from Radi Medical Systems, Uppsala, Sweden, a second input data signal 120 representing hemodynamic data, such as the intravascular may be obtained. Further, a system with guide-wire with pressure sensor is disclosed in U.S. Pat. No. 6,565,514 and WO 06/041346. In US 2007/255145 a guide-wire with pressure sensor is being disclosed.

In intravascular ultrasound (IVUS) imaging the physician positions the tip of a guide-wire, usually 0.36 mm (0.014") diameter with a very soft and pliable tip and about 200 cm long, in a blood vessel branch. The physician steers the guide-wire from outside the body, through angiography catheters and into the blood vessel branch to be imaged. Once in position, an ultrasound catheter tip is slid in over the guide-wire and positioned, using angiography techniques, so that the tip is at the farthest away position to be imaged. The ultra sound waves emitted from the catheter tip are usually in the 20-40 MHz range. The catheter also receives and conducts the return echo information out to an external computerized ultrasound equipment, which constructs, and possibly also displays, a real time ultrasound image of a thin section of the blood vessel currently surrounding the catheter tip. Typically, the displayed image is a 30 frames/second image.

As already disclosed, the second input data 120 may typically be a real time ultrasound image signal from a computerized ultrasound equipment.

Figure 2:
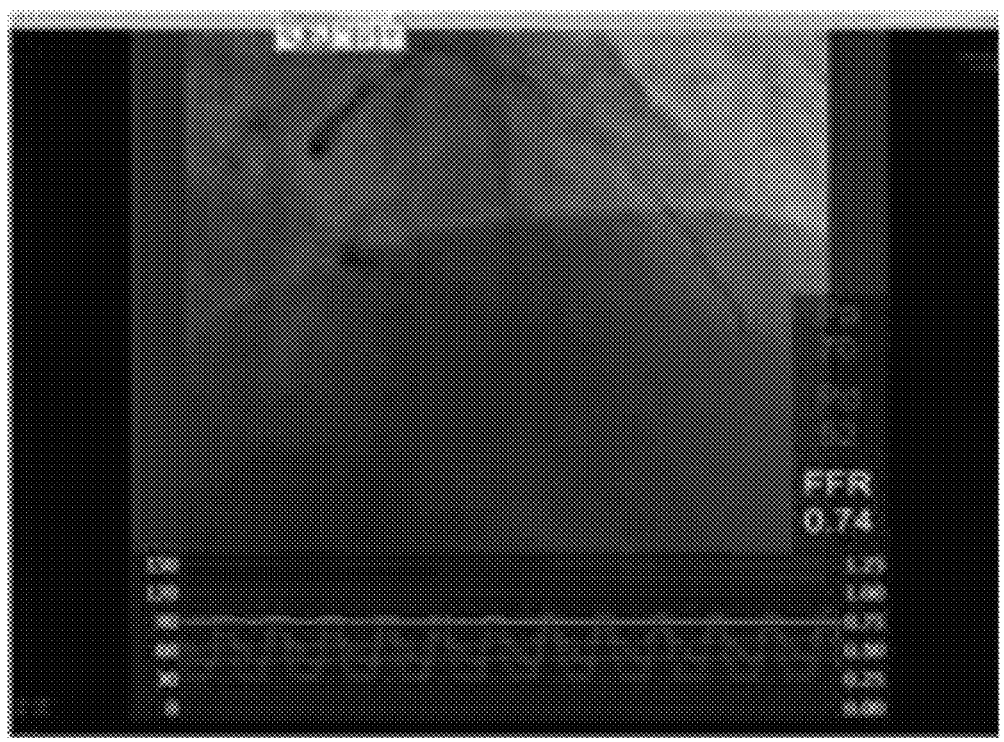
FIG. 2 depicts an example of a synchronous representation of X-ray imaging data and intra vascular hemodynamic parameter data displayed as a graph over time of the intra vascular pressure and as the Fractional Flow Reserve (FFR).

The system 100 allows for displaying of a synchronous representation of a graph showing the intravascular pressure and an X-ray angiography imaging signal (cf. FIG. 2), whereby the physician may determine the position of a stenosis within a coronary artery. Further, the representation displayed may also include FFR, thus also the severity of the stenosis may be assessed.

Evidently, the system 100 allows for various types of synchronous representation. Further, as will be outlined below, the system 100 is provided with an input device 150. The input device 150 and the control unit 130 may be arranged to allow for switching between various predefined representation outlays being displayed on the display unit 140. A switch between different outlays allows for focusing on the X-ray angiography imaging in guiding the probe to the coronary artery, in which the measurement is to be made. Once the probe is positioned in the coronary artery of interest, a representation outlay focusing of the graph showing the intravascular pressure and other relevant parameters such as FFR may selected by the examining physician via the input device 150. Thus, the visualization provided by the system 100 via the display unit 140 may be optimized for different parts of the examination providing the physician with valuable assistance.

As already stated, the system 100 may be provided with an input device 150. The input device 150 may be a physically separate device, such as a keypad, keyboard, multi-switch panel or other device capable of receiving commands as input by a user. Alternatively, in some embodiments it may be integrated in the display unit 140. In such embodiments, the display unit 140 may advantageously be implemented as a touch screen, i.e. a display device which is also capable of acting as the input device 150 by detecting user actuation on the display surface through capacitive, resistive, optical or other sensor means. The input device 150 communicates with the control unit 130. As already described, the input device 150 may be used to select what representation outlay to be presented on the display unit 140.

The control unit may for instance be implemented by any commercially available central processing unit (CPU) or digital signal processor (DSP), or other programmable electronic logic device such as an application-specific integrated circuit (ASIC) or field-programmable gate array (FPGA).

The system 100 may also be provided with a memory unit 160. The memory unit 160 may be arranged for storing a snap shot of a representation outlay displayed on the display unit 140. Accordingly, the memory unit 160 communicates with the control unit 130. By use of the input device 150, the physician may command the control unit 130 to store a snap shot of the representation outlay displayed on the display unit 140 in the memory unit 160.

Further, the memory unit 160 may also be arranged for recording a dynamic sequence of images of the displayed outlay of the representation of the first and second input data 110 and 120 as a recording. As the representation of the first and second input data 110, 120 is a synchronous representation in real time, the representation of the first and second input data 110 and 120 are inherently synchronized. Thereby, the recording stored in the memory unit 160 will represent a playback of the examination. By use of the input device 150, the physician may command the control unit 130 to start and stop the recording of the representation outlay displayed on the display unit 140 in the memory unit 160. Thus, only relevant parts of the examination may be recorded and stored.

The memory unit 160 may for instance be implemented by any commercially available storage memory technology, such as for instance EEPROM, flash memory, hard disk, or any combination thereof.

According to a further embodiment (cf. FIG. 1), the control unit 130 of the system, described herein above, may be connected to a data network 200. The data network 200 may be local area network (LAN) at a hospital. Further, the LAN may be connected to the Internet or any other kind of wide area network (WAN). The networks 200 may be wired, wireless or a combination thereof.

Via the network 200, the snap shot and/or the recording may be sent to a server 300 also connected to the network 200. Further, the input device 150 may be used to commanding the control unit 130 to send the snap shot and/or the recording stored in the memory unit 160 to the server 300. In the server 300, the snap shot and/or the recording may be stored in a database 310 being contained in, coupled to or otherwise associated with the server 300. The database 310 may for instance have a relational database model or an object database model. The server 300 may access the database 310 through one or more data access interfaces, such as Structured Query Language (SQL).

Figure 4:
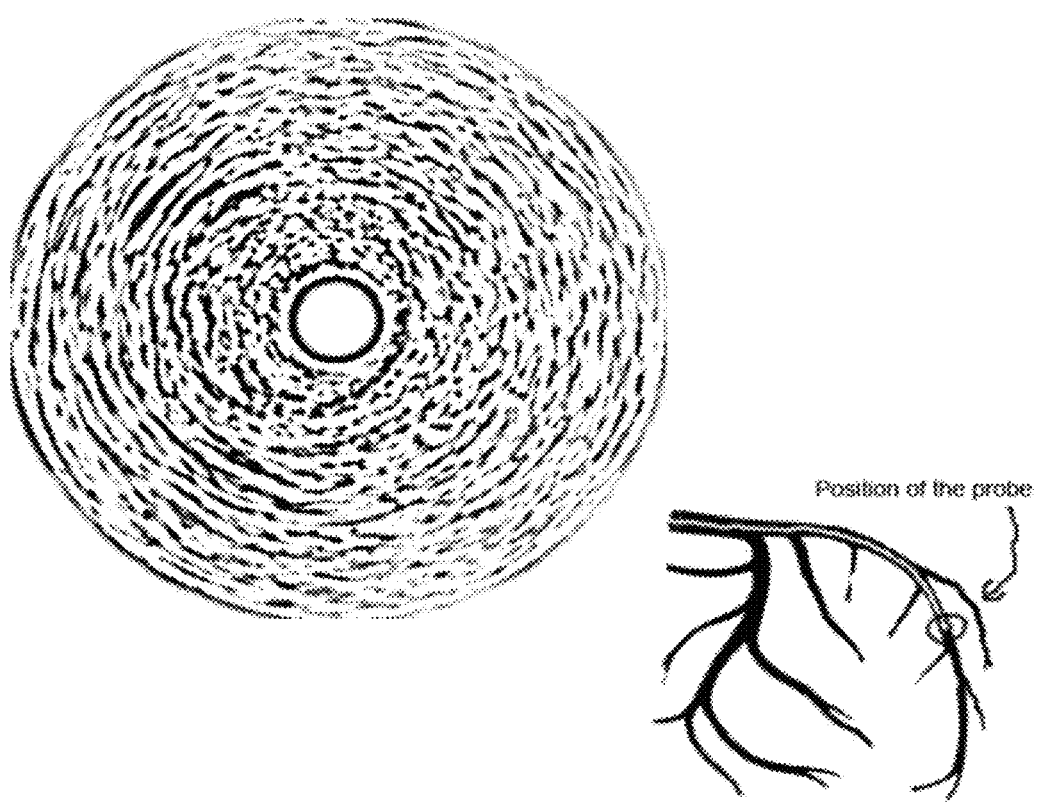
FIG. 4 depicts an example of a synchronous representation of X-ray imaging data and intravascular ultrasound (IVUS) imaging data, wherein also patient specific data is being displayed. The position of the ultrasound probe is indicated in the figure.

Further, the database is typically a database of case records, such as a Picture Archiving and Communication System (PACS). Via the input device 150, also patient specific data, such as data allowing for identifying the patient being examined, e.g. a personal code number or social security number, may be stored in the database 310. Other examples of patient specific data are the date of the examination and other data relating to the examination. Additionally, such further data may be displayed on the display unit 140 together with the synchronous representation (cf. FIG. 4) of the first and second input data 110, 120.

As the server 300, with the database 310, is connected to a network, the snap shot and/or the recording stored in the database may be subsequently accessed via workstation(s) 400 connected to the network 200.

More importantly, storage of the snap shot and/or the recording in the database 310 allows for evaluation of the examination afterwards. As the stored recording is an exact playback of the examination, it is possible to scrutinize the diagnosis set by the physician without having to repeat the examination. This is important for patient security. Further, the stored recording may be valuable in teaching.

The possibility to scrutinize the diagnosis, or for the examining physician to justify it, afterwards is very valuable as the costs for health care are increasing rapidly, especially in the western parts of the world. There is therefore a demand for a reliable and efficient way of archiving examination results from examinations of coronary artery diseases, which the present system seeks to meet.

Figure 3:
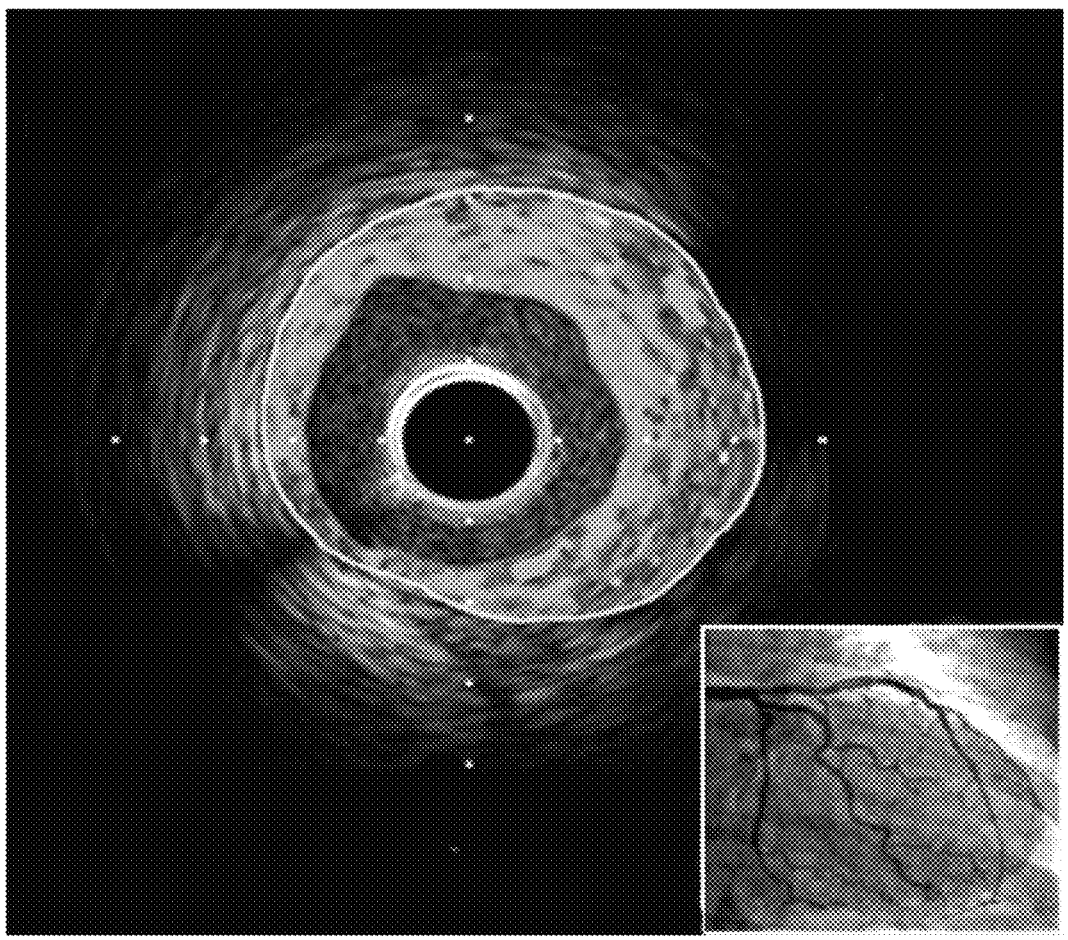
FIG. 3 depicts an example of a synchronous representation of X-ray imaging data and intravascular ultrasound (IVUS) imaging data.

Another embodiment relates to a method of synchronously visualizing X-ray imaging data and intra vascular hemodynamic data or intravascular ultrasound (IVUS) imaging data. In such a method, X-ray imaging data and intra vascular hemodynamic data or intravascular ultrasound (IVUS) imaging data are being collected. Herein above, collection of such data is described. As already outlined, the collected X-ray imaging data typically allows for determining the position of a probe used to collect the intra vascular hemodynamic data, such as the intra vascular pressure, or the intravascular ultrasound (IVUS) imaging data. The collected data is subsequently processed. Procession of the collected data may be affected by a control unit 130, which receives the collected data 110, 120. The processed data is then displayed as a synchronous common representation of the collected data. A display unit 140 may be used to display the processed data. While the X-ray imaging data may be displayed as an image updated in real time (e.g. an image of 30 frames/second), the intra vascular hemodynamic data may typically be displayed as pressure graph and optionally also FFR (cf. FIG. 2). Also the intravascular ultrasound (IVUS) imaging data may be displayed (cf. FIG. 3) as an image updated in real time (e.g. an image of 30 frames/second).

From the displayed representation of the collected data, a physician may accurately, and in real time, determine relevant cardio vascular parameters, such as the intravascular pressure or the presence of atheromatous plaque, at a given position apparent from the displayed X-ray angiography imaging.

Further, the method may comprise the step of storing a snap shot of the displayed representation of the X-ray imaging data and the intra vascular hemodynamic data or the intravascular ultrasound (IVUS) imaging data. The snap shot may be stored on a memory unit 160. By using an input device 150, such as keyboard or a touch-screen, the physician may command the control unit 130 to store the snap shot on the memory unit 160 during the examination.

Similarly the method may comprise the step of recording a dynamic sequence of images of the displayed representation of X-ray imaging data and intra vascular hemodynamic data or intravascular ultrasound (IVUS) imaging data. By using an input device 150, the physician may command the control unit 130 to store to store the recording on the memory unit 160 during the examination.

The method may further comprise the step of selecting the outlay of the representation of X-ray imaging data and intra vascular hemodynamic data or intravascular ultrasound (IVUS) imaging data to be displayed. Typically, the outlay may be selected from predefined outlays. Thus, the examining physician may switch between various predefined outlays during the examination, which may facilitate the examination.

As already outlined, the control unit 130 may be connected to a data network 200. As the data being collected and displayed is medical (imaging) data, the data network 200 is typically an local area network (LAN) at a hospital. The method may further comprise the step of archiving the stored snap shot and/or recording. Archiving of data is a common procedure at hospitals and medical data is typically archived in a database also comprising patient information, such as a Picture Archiving and Communication System (PACS).

Accordingly, the stored snap shot and/or recording may be archived in a database 310 contained in, coupled to or otherwise associated with the server 300. The stored snap shot and/or recording to be archived may be send to a server 300 also connected to the network 200. Via the input device 150, the physician may archive the stored snap shot and/or recording in the database 310. Further, also patient specific data, allowing for identifying the patient being examined, e.g. a personal code number or social security number, may be archived by entering it via the input device 150. Additionally, the patient specific data may be displayed along with the visualization of the X-ray imaging data and the intra vascular hemodynamic data or the intravascular ultrasound (IVUS) imaging data.

Without further elaboration, it is believed that one skilled in the art may, using the preceding description, utilize the present invention to its fullest extent. The following preferred specific embodiments are, therefore, to be construed as merely illustrative and not limitative of the remainder of the disclosure in any way whatsoever.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do not preclude a plurality.

The invention claimed is:

1. A method of synchronously visualizing X-ray imaging data and at least one of intra vascular hemodynamic parameter data and intra vascular hemodynamic image data, the method comprising:

collecting X-ray imaging data and at least one of intra vascular hemodynamic parameter data and intra vascular hemodynamic image data from a patient;

processing the collected data; and displaying the processed data as a synchronous common representation of the collected data;

wherein the representation of the intra vascular hemodynamic parameter data displayed is at least one of a graph of a plurality of data points over a period of time of the intra vascular pressure and the Fractional Flow Reserve (FFR) at a given location; and wherein collecting at least one of intra vascular hemodynamic parameter data and intra vascular hemodynamic image data involves taking measurements using a guide wire inserted into the patient.

2. The method according to claim 1, further comprising at least one of:

storing a snap shot of the displayed representation of the X-ray imaging data and at least one of the intra vascular hemodynamic parameter data and the intra vascular hemodynamic image data; and recording a dynamic sequence of images of the displayed representation of X-ray imaging data and at least one of intra vascular hemodynamic parameter data and intra vascular hemodynamic image data.

3. The method according to claim 1, further comprising:

selecting the outlay of the representation of X-ray imaging data and at least one of intra vascular hemodynamic parameter data and intra vascular hemodynamic image data to be displayed.

4. The method according to claim 2, further comprising:

archiving the stored snap shot and/or the recording in a database.

5. The method according to claim 4, further comprising:

archiving patient specific data, allowing for identifying the patient from which the X-ray imaging data and at least one of intra vascular hemodynamic parameter data and intra vascular hemodynamic image data is being collected, together with the stored snap shot and/or the recording in a database.

* * * * *